United States Patent
Bauer et al.

(10) Patent No.: US 9,434,802 B2
(45) Date of Patent: Sep. 6, 2016

(54) METHOD FOR REMOVAL OF RESIDUAL MONOMERS FROM WATER-ABSORBING POLYMER PARTICLES

(71) Applicant: BASF SE, Ludwigshafen (DE)

(72) Inventors: Stephan Bauer, Hochheim (DE); Norbert Herfert, Altenstadt (DE); Lydia König, Harthausen (DE); Yvonne Hagen, Waldsee (DE); Xiana Romani Fernandez, Karlsruhe (DE); Marcus Schöppler, Altlussheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/762,026

(22) PCT Filed: Jan. 20, 2014

(86) PCT No.: PCT/EP2014/050988
§ 371 (c)(1),
(2) Date: Jul. 20, 2015

(87) PCT Pub. No.: WO2014/118025
PCT Pub. Date: Aug. 7, 2014

(65) Prior Publication Data
US 2015/0322188 A1 Nov. 12, 2015

(30) Foreign Application Priority Data
Jan. 30, 2013 (EP) ..................... 13153279

(51) Int. Cl.
*C08F 4/00* (2006.01)
*C08F 30/04* (2006.01)
(Continued)

(52) U.S. Cl.
CPC .............. *C08F 220/06* (2013.01); *A61L 15/24* (2013.01); *A61L 15/60* (2013.01); *C08F 6/005* (2013.01); *C08F 6/008* (2013.01); *C08L 33/02* (2013.01); *C08L 2201/54* (2013.01)

(58) Field of Classification Search
CPC ....... A61L 15/60; A61L 33/02; A61L 15/24; C08F 6/005; C08F 6/008; C08F 220/06; C08L 2201/54; C08L 2312/00
USPC .............. 526/240, 235, 219.2, 317.1, 318.42
See application file for complete search history.

(56) References Cited

U.S. PATENT DOCUMENTS 8,299,207 B2 * 10/2012 Wengeler ................ C08F 6/005
428/402
2010/0035059 A1    2/2010 Losch et al.
(Continued)

FOREIGN PATENT DOCUMENTS

WO    WO-2008/092843 A1    8/2008
WO    WO-2008/095901 A1    8/2008
(Continued)

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.

(Continued)

*Primary Examiner* — William Cheung
(74) *Attorney, Agent, or Firm* — Marshall, Gerstein & Borun LLP

(57) ABSTRACT

A process for removing residual monomers from water-absorbing polymer particles by thermally aftertreating the water-absorbing polymer particles in a mixer with rotating mixing tools at a temperature of at least 60° C. in the presence of water and of a surfactant.

15 Claims, 3 Drawing Sheets

(51) Int. Cl.

| | |
|---|---|
| *C08F 2/00* | (2006.01) |
| *C08F 20/26* | (2006.01) |
| *C08F 220/06* | (2006.01) |
| *A61L 15/24* | (2006.01) |
| *A61L 15/60* | (2006.01) |
| *C08F 6/00* | (2006.01) |
| *C08L 33/02* | (2006.01) |

(56) References Cited

U.S. PATENT DOCUMENTS

2010/0041550 A1 2/2010 Riegel et al.
2011/0059329 A1 3/2011 Dobrawa et al.
2011/0136986 A1 6/2011 Elliott et al.
2011/0237767 A1 9/2011 Wengeler et al.

FOREIGN PATENT DOCUMENTS

WO WO-2010/018143 A1 2/2010
WO WO-2011/117215 A1 9/2011

OTHER PUBLICATIONS

International Search Report for International Application No. PCT/EP2014/050988, dated May 16, 2014 (translation).

\* cited by examiner

METHOD FOR REMOVAL OF RESIDUAL MONOMERS FROM WATER-ABSORBING POLYMER PARTICLES

CROSS-REFERENCE TO RELATED APPLICATIONS

This application is the U.S. National Phase of PCT Application No. PCT/EP2014/050988, filed Jan. 20, 2014, which claims the benefit of European patent application No. 13153279.8, filed Jan. 30, 2013.

The present invention relates to a process for removing residual monomers from water-absorbing polymer particles by thermally aftertreating the water-absorbing polymer particles in a mixer with rotating mixing tools at a temperature of at least 60° C. in the presence of water and of a surfactant.

The production of water-absorbing polymer particles is described in the monograph "Modern Superabsorbent Polymer Technology", F. L. Buchholz and A. T. Graham, Wiley-VCH, 1998, pages 71 to 103.

Being products which absorb aqueous solutions, water-absorbing polymers are used to produce diapers, tampons, sanitary napkins and other hygiene articles, but also as water-retaining agents in market gardening. Water-absorbing polymers are also referred to as "superabsorbent polymers" or "superabsorbents".

WO 2008/095901 A1 describes a process for removing residual monomers by thermal aftertreatment with steam in the fluidized state.

WO 2011/117215 A1 describes a process for removing residual monomers from water-absorbing polymer particles, wherein the water-absorbing polymer particles are thermally aftertreated in a mixer with rotating mixing tools at a temperature of at least 60° C. in the presence of steam.

It was an object of the present invention to provide an improved and gentle process for removing residual monomers from water-absorbing polymer particles. More particularly, the formation of agglomerates is to be prevented or at least suppressed at relatively high water contents.

Agglomerates refer to particles which consist of at least two primary particles bonded to one another and are formed during the thermal aftertreatment step and have a particle size of greater than 850 µm.

The object was achieved by a process for removing residual monomers from water-absorbing polymer particles by thermally aftertreating the water-absorbing polymer particles in a mixer with rotating mixing tools, the water-absorbing polymer particles during the thermal aftertreatment having a temperature of at least 60° C. and a water content of at least 8% by weight, with addition of water or an aqueous solution before or during the thermal aftertreatment and/or of a steam-comprising gas stream during the thermal aftertreatment, which process comprises performing the thermal aftertreatment in the presence of at least one surfactant, the at least one surfactant having a polar group and a nonpolar group, the polar group and the nonpolar group of the surfactant not being joined via a carboxylic ester group, and the polar group having at least one hydroxyl group, a cationic group or an anionic group and the nonpolar group having a $C_4$- to $C_{20}$-alkyl chain.

The temperature of the water-absorbing polymer particles during the thermal aftertreatment is preferably from 60 to 140° C., more preferably from 70 to 125° C. and very particularly from 80 to 110° C.

The water content of the water-absorbing polymer particles during the thermal aftertreatment is preferably from 8 to 50% by weight, more preferably from 12 to 30% by weight and most preferably from 15 to 22% by weight.

Preferred polar groups are cationic groups. Additionally preferred are surfactant mixtures. The surfactant mixtures preferably comprise surfactants having different linear and/or branched alkyl chains as nonpolar groups. Particular preference is given to surfactant mixtures whose alkyl chains derive from coconut oil, i.e. surfactant mixtures with $C_6$, $C_8$, $C_{10}$, $C_{12}$, $C_{14}$, $C_{16}$ and $C_{18}$ alkyl chains.

The present invention is based on the finding that the formation of agglomerates can be lowered by adding particular surfactants as deagglomeration assistants. It appears to be essential that the polar group and the nonpolar group of the surfactant remain joined even under the conditions of the thermal aftertreatment. Surfactants having a hydrolysis-sensitive carboxylic ester group at this position are unsuitable.

Suitable surfactants or surfactant mixtures are:
a) Alkyl glycosides and polyglycosides, for example lauryl glycoside, cocoglycoside and surfactant mixtures comprising these compounds. Surfactants of this kind are obtainable under the trade names Plantacare® (BASF SE) and Euperlan® (BASF SE) and Lutensol®GD (BASF SE). Examples include cocoglycoside (Plantacare®818UP, BASF SE, CAS No. 110615-47-9/68515-73-1), lauryl glycoside (Plantacare®1200UP, BASF SE, CAS No. CAS No. 110615-47-9), mixtures of lauryl glycoside and cocoamidopropyl betaine (Plantacare®K55, BASF SE, CAS No. CAS No. 110615-47-9/61789-40-0), mixtures of sodium laureth sulfate and lauryl glycoside (Plantacare®PS10, BASF SE, CAS No. CAS No. 110615-47-9/68891-38-3), pearlescent wax dispersions comprising lauryl glycoside and stearyl citrate (Euperlan®Green, BASF SE, CAS No. CAS No. 110615-47-9/1337-33-4), styrene/acrylate dispersion comprising cocoglycoside (Euperlan®PCO, BASF SE).
b) Ethoxylated alkyl alcohols of the general structure $H_{2n+1}C_nO(C_2H_4O)_nH$, especially fatty alcohols, oxo alcohols, Guerbet alcohols. Surfactants of this kind are obtainable under the trade names Lutensol®AT, AO, TO, XP, XL, XA, ON (BASF SE).
c) Ethoxylated alkylphenols, for example Lutensol®AP (BASF SE).
d) Ethoxylated castor oil, for example Emulan® (BASF SE).
e) Ethoxylated alkylamides, for example oleylamide, cocoamide, oleamide. Surfactants of this kind are obtainable under the trade names Lutensol® FA and FSA (BASF SE).
f) Cationic surfactants, for example benzalkonium chloride, benzyldimethyldodecylammonium chloride, benzyldimethylammonium chloride, myristalkonium chloride, cetalkonium chloride, benzyldimethylstearylammonium chloride, benzyldimethylstearylammonium chloride, didecyldimethylammonium chloride, didodecyldimethylammonium chloride, dimethylditetradecylammonium chloride, dihexadecyldimethylammonium chloride, dimethyldioctadecylammonium chloride, ditallowdimethylammonium chloride, hexadecyl(2-hydroxyethyl)dimethylammonium dihydrogenphosphate, very preferably hexadecyl(2-hydroxyethyl)dimethylammonium dihydrogenphosphate, obtainable under the trade name Luviquat®Mono CP (BASF SE).

Very preferred are lauryl glycoside, cocoglycoside, ditallowdimethylammonium chloride and hexadecyl(2-hydroxyethyl)dimethylammonium dihydrogenphosphate.

The surfactant is used in an amount of preferably 0.0001 to 0.1% by weight, more preferably 0.0002 to 0.05% by weight, most preferably 0.0005 to 0.01% by weight, based in each case on the water-absorbing polymer particles.

The surfactant lowers the surface tension of the aqueous extract and can thus increase the leakage rate of diapers. The surfactant is therefore advantageously dosed such that the surface tension of the aqueous extract falls by not more than 10 mN/m. To measure the surface tension of the aqueous extract, 2 g of water-absorbing polymer particles are swollen in a beaker with sufficient water that there is a water layer of thickness about 1 cm above the hydrogel which forms. Subsequently, the surface tension of the water is measured with a tensiometer.

Before or during the thermal aftertreatment, it is possible to add water or an aqueous solution, preferably from 0.01 to 25% by weight, more preferably from 0.05 to 20% by weight and most preferably from 0.1 to 15% by weight, based in each case on the water-absorbing polymer particles. The temperature of the water or of the aqueous solution is preferably from 1 to 99° C., more preferably from 20 to 80° C. and most preferably from 40 to 70° C. The temperature of the water-absorbing polymer particles before the spray application of the water or of the aqueous solution is in the range from preferably 1 to 160° C., more preferably 20 to 120° C., especially preferably 30 to 100° C. and most preferably 60 to 90° C. Advantageously, the water or the aqueous solution is applied by means of a plurality of nozzles in a suitable mixer.

During the thermal aftertreatment, a steam-comprising gas stream may be added. The gas stream comprises preferably from 0.01 to 2.0 kg of steam per kg of dry gas, more preferably from 0.05 to 1.0 kg of steam per kg of dry gas and most preferably from 0.1 to 0.5 kg of steam per kg of dry gas.

The mean residence time in the mixer during the thermal aftertreatment is preferably from 10 to 120 minutes, more preferably from 12 to 100 minutes, especially preferably from 15 to 90 minutes and most preferably from 20 to 40 minutes.

The gas volume used for thermal aftertreatment in a batchwise mixer is preferably from 0.01 to 5 m³ (STP)/h, more preferably from 0.05 to 2 m³ (STP)/h and most preferably from 0.1 to 0.5 m³ (STP)/h, in each case per kg of water-absorbing polymer particles, and, in a continuous mixer, preferably from 0.01 to 5 m³ (STP)/h, more preferably from 0.05 to 2 m³ (STP)/h and most preferably from 0.1 to 0.5 m³ (STP)/h, in each case per kg/h of water-absorbing polymer particle throughput. The gas volume here is the gas volume corrected to standard conditions (0° C.; 1013.25 hPa).

The remaining constituents of the gas are preferably nitrogen, carbon dioxide, argon, xenon, krypton, neon, helium, air or air/nitrogen mixtures, more preferably nitrogen or air/nitrogen mixtures containing less than 10% by volume of oxygen.

The presence of oxygen can lead to discoloration of the water-absorbing polymer particles. Air, in contrast, is particularly inexpensive.

In the process according to the invention, it is possible to use all batchwise and continuous mixers which have rotating mixing tools and are known to those skilled in the art, such as screw mixers, disk mixers, helical ribbon mixers and paddle mixers. Suitable mixers are, for example, Becker Shovel Mixers (Gebr. Lödige Maschinenbau GmbH; Paderborn; Germany), Nara Paddle Mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Ruberg GmbH & Co KG; Nieheim; Germany). In the process according to the invention, preference is given to using Becker Shovel Mixers, Pflugschar® plowshare mixers and Ruberg continuous flow mixers for thermal aftertreatment.

Mixers with rotating mixing tools are divided into vertical mixers and horizontal mixers according to the position of the axis of rotation. Advantageously, horizontal mixers are used for the process according to the invention.

Horizontal mixers in the context of this invention are mixers with rotating mixing tools, the position of which with respect to the product flow direction deviates from the horizontal by less than 20°, preferably by less than 15°, more preferably by less than 10° and most preferably by less than 5°.

For mixers with horizontally mounted mixing tools, the Froude number is defined as follows:

$$Fr = \frac{\omega^2 r}{g}$$

where
r: radius of the mixing tool
ω: angular frequency
g: acceleration due to gravity The Froude number is preferably from 0.1 to 6, more preferably from 0.15 to 3 and most preferably from 0.2 to 1.

The inner wall of the mixer has, with respect to water, a contact angle of preferably less than 70°, more preferably of less than 60° and most preferably of less than 50°. The contact angle is a measure of the wetting behavior and is measured to DIN 53900.

It is advantageous in the process according to the invention to use mixers whose inner wall which is in contact with the product is made of a stainless steel. Stainless steels typically have a chromium content of 10.5 to 13% by weight. The high chromium content leads to a protective passivation layer of chromium dioxide on the steel surface. Further alloy constituents increase the corrosion resistance and improve the mechanical properties.

Particularly suitable steels are austenitic steels with, for example, at least 0.08% by weight of carbon. The austenitic steels advantageously comprise further alloy constituents, preferably niobium or titanium, in addition to iron, carbon, chromium, nickel and optionally molybdenum.

The preferred stainless steels are steels with materials number 1.43xx or 1.45xx according to DIN EN 10020, where xx may be a natural number from 0 to 99. Particularly preferred materials are the steels with materials numbers 1.4301, 1.4541 and 1.4571, especially steel with materials number 1.4301.

Advantageously, the inner wall of the mixer which is in contact with the product is polished or electropolished. Polished stainless steel surfaces have a lower roughness and a lower contact angle with respect to water than matt or roughened steel surfaces.

In one embodiment of the process, the mixer is equipped with a nonstick coating, for example with polytetrafluoroethylene (PTFE), a nickel-phosphorus alloy with embedded polytetrafluoroethylene particles (Ni-PTFE), polyvinylidene fluoride (PVDF) or another suitable polymer, for example with hydrophobic polymers such as silicones, or a chemical vapor deposition (CVD) coating. The latter is described in the conference paper by S. Montgomery, D. Kennedy, N. O'Dowd, "PVD and CVD Coating for the Metal Forming Industry", Matrib 2010, Croatia.

The production of the water-absorbing polymer particles is described hereinafter:

The water-absorbing polymer particles are produced, for example, by polymerizing a monomer solution comprising:
a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a),
e) optionally one or more water-soluble polymers or copolymers and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid, vinylsulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The acid groups of the monomers a) have typically been partially neutralized, preferably to an extent of at least 25 mol %, more preferably to an extent of 50 to 80 mol %, especially preferably 60 to 75 mol % and most preferably 65 to 72 mol %, for which the customary neutralizing agents can be used, preferably alkali metal hydroxides, alkali metal oxides, alkali metal carbonates or alkali metal hydrogencarbonates, and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and mixtures thereof. Typically, neutralization is achieved by mixing in the neutralizing agent in the form of an aqueous solution, in the form of a melt, or else preferably in solid form. For example, sodium hydroxide with a water content significantly below 50% by weight may be present as a waxy material with a melting point above 23° C. In this case, metered addition as piece material or a melt at elevated temperature is possible.

Optionally, one or more chelating agents may be added to the monomer solution or starting materials thereof to mask metal ions, for example iron, for the purpose of stabilization. Suitable chelating agents are, for example, alkali metal citrates, citric acid, alkali metal tartrates, pentasodium triphosphate, ethylenediamine tetraacetate, nitrilotriacetic acid, and also all chelating agents known by the Trilon® name, for example Trilon® C (pentasodium diethylenetriaminepentaacetate), Trilon® D (trisodium (hydroxyethyl) ethylenediaminetriacetate), and Trilon® M (methylglycinediacetic acid).

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic or methacrylic acid to give di- or triacrylates, as described, for example, in WO 2003/104301 A1. Di- and/or triacrylates of 3- to 20-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ (AUL0.3psi) passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, maleic acid, fumaric acid, dimethylaminoethyl methacrylate, dimethylaminoethyl acrylate, dimethylaminopropyl acrylate, diethylaminopropyl acrylate, dimethylaminoethyl methacrylate and diethylaminoethyl methacrylate.

The water-soluble polymers or copolymers e) used may be polyvinyl alcohol, polyvinylpyrrolidone, polyvinylamines, polyallylamines, polyethyleneimines, polyacrylamide, linear hydrophobic polyurethanes, starch, starch derivatives, modified cellulose, such as methyl cellulose or hydroxyethyl cellulose, gelatin, polyethylene glycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors (gel polymerization). In the kneader, the polymer gel formed in the polymerization of an aqueous monomer solution is comminuted continuously by, for example, contrarotatory stirrer shafts, as described in WO 2001/38402 A1. Polymerization on a belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

When kneading reactors or belt reactors are used, it is possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The resulting polymer gel is preferably dried with a belt drier until the residual moisture content is preferably 0.5 to 15% by weight, more preferably 1 to 10% by weight and most preferably 2 to 8% by weight, the residual moisture content being determined by EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Thereafter, the dried polymer gel is ground and classified, and the apparatus used for grinding may typically be single or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm and very particularly from 300 to 500 μm. The mean particle size of the product fraction may be determined by means of EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles ("fines") should therefore be low.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or may be coated in another way, for example with fumed silica.

If a kneading reactor is used for polymerization, the excessively small polymer particles are preferably added during the last third of the polymerization.

If the excessively small polymer particles are added at a very early stage, for example actually to the monomer solution, this lowers the centrifuge retention capacity (CRC) of the resulting water-absorbing polymer particles. However, this can be compensated for, for example, by adjusting the amount of crosslinker b) used.

If the excessively small polymer particles are added at a very late stage, for example not until an apparatus connected downstream of the polymerization reactor, for example an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight and most preferably at least 98% by weight.

Polymer particles of excessively large particle size lower the free swell rate. The proportion of excessively large polymer particles should therefore likewise be low.

Excessively large polymer particles are therefore typically removed and recycled into the grinding of the dried polymer gel.

However, it is also possible to dropletize an aqueous monomer solution and to polymerize the droplets obtained in a heated carrier gas stream. It is possible here to combine the process steps of polymerization and drying, as described in WO 2008/052971 A1 and WO 2011/026876 A1.

For this purpose, the monomer solution is metered into the reaction chamber by means of at least one hole to form droplets. The holes may, for example, be in a dropletizer plate.

A dropletizer plate is a plate with at least one hole, the liquid passing through the hole from the top. The dropletizer plate or the liquid can be oscillated, which generates a chain of ideally monodisperse droplets at each hole on the underside of the dropletizer plate. In a preferred embodiment, the dropletizer plate is not agitated.

The number and size of the holes are selected according to the desired capacity and droplet size. The droplet diameter is typically 1.9 times the diameter of the hole. What is important here is that the liquid to be dropletized does not pass through the hole too rapidly and the pressure drop across the hole is not too great. Otherwise, the liquid is not dropletized, but rather the liquid jet is broken up (sprayed) owing to the high kinetic energy. The Reynolds number based on the throughput per hole and the hole diameter is preferably less than 2000, more preferably less than 1600, especially preferably less than 1400 and most preferably less than 1200.

The underside of the dropletizer plate has a contact angle with respect to water of preferably at least 60°, more preferably at least 75° and most preferably at least 90°.

The contact angle is a measure of the wetting characteristics of water with respect to a surface and can be determined by customary methods, for example to ASTM D 5725. A low contact angle means good wetting and a high contact angle poor wetting.

However, it is also possible that the dropletizer plate consists of a material with a relatively low contact angle with respect to water, for example a steel with materials number 1.4571, and is coated with a material having a greater contact angle with respect to water.

Suitable coatings are, for example, fluorinated polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings may also be applied in the form of a dispersion, in which case the dispersant evaporates in the course of the subsequent heating. Such a process is described, for example, in U.S. Pat. No. 3,243,321.

Further coating processes can be found under the heading "Thin Films" in the electronic version of "Ullmann's Encyclopedia of Industrial Chemistry".

However, the coating may also be a nickel layer produced by chemical nickel plating.

Owing to the poor wettability of the dropletizer plate, monodisperse droplets with narrow droplet size distribution are obtained.

The dropletizer plate has preferably at least 5, more preferably at least 25 and most preferably at least 50 holes, and preferably up to 750, more preferably up to 500 and most preferably up to 250 holes. The diameter of the holes is selected according to the desired droplet size.

The diameter of the holes is preferably from 50 to 500 μm, more preferably from 100 to 300 μm and most preferably from 150 to 250 μm.

The temperature of the monomer solution on passage through the holes is preferably from 5 to 80° C., more preferably from 10 to 70° C. and most preferably from 30 to 60° C.

The distance between the holes is preferably 10 to 50 mm, more preferably 12 to 40 mm and most preferably 15 to 30 mm. Excessively small distances lead to formation of agglomerates.

A carrier gas flows through the polymerization reactor. This carrier gas can be conducted through the reaction chamber in cocurrent or in countercurrent to the free-falling droplets of the monomer solution, preferably in cocurrent, i.e. from the bottom upward. After one pass, the carrier gas is preferably recycled at least partly into the reaction chamber as cycle gas, preferably to an extent of at least 50% and more preferably to an extent of at least 75%. Typically, a portion of the carrier gas is discharged after each pass, preferably up to 10%, more preferably up to 3% and most preferably up to 1%.

The oxygen content of the carrier gas is preferably from 0.5 to 15% by volume, more preferably from 1 to 10% by volume and most preferably from 2 to 7% by weight.

As well as oxygen, the carrier gas preferably comprises nitrogen. The nitrogen content of the carrier gas is preferably at least 80% by volume, more preferably at least 90% by volume and most preferably at least 95% by volume. Further suitable carrier gases are carbon dioxide, argon, xenon, krypton, neon and helium. It is also possible to use gas mixtures. The carrier gas may also be laden with steam and/or acrylic acid vapors.

The gas velocity is preferably set such that the flow in the polymerization reactor is directed, for example no convection currents opposed to the general flow direction are present, and is typically 0.1 to 2.5 m/s, preferably 0.3 to 1.5 m/s, more preferably from 0.5 to 1.2 m/s, especially preferably 0.6 to 1.0 m/s and most preferably 0.7 to 0.9 m/s.

The carrier gas flowing through the reactor is appropriately preheated to the reaction temperature upstream of the reactor.

Advantageously, the gas inlet temperature is regulated such that the gas outlet temperature, i.e. the temperature with which the carrier gas leaves the reaction chamber, is typically from 90 to 150° C., preferably from 100 to 140° C., more preferably from 105 to 135° C., especially preferably from 110 to 130° C. and most preferably from 115 to 125° C.

The reaction can be performed under elevated pressure or under reduced pressure; a reduced pressure of down to 100 mbar relative to ambient pressure is preferred.

The reaction offgas, i.e. the gas leaving the reaction chamber, can, for example, be cooled in a heat exchanger. This condenses water and unconverted monomer a). Thereafter, the reaction offgas can at least partly be reheated and recycled into the reactor as cycle gas. A portion of the reaction offgas can be discharged and replaced by fresh carrier gas, in which case water and unconverted monomers a) present in the reaction offgas can be removed and recycled.

Particular preference is given to an integrated heating system, which means that some of the waste heat in the cooling of the offgas is used to heat the cycle gas.

The reactors may be trace-heated. The trace heating is adjusted such that the wall temperature is at least 5° C. above the internal reactor temperature, and condensation at the reactor walls is reliably prevented.

The reaction product is subsequently thermally aftertreated and optionally dried down to the desired water content.

To further improve the properties, the water-absorbing polymer particles may be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are ethylene carbonate, 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001 to 5% by weight, more preferably 0.02 to 2.5% by weight, more preferably 0.03 to 1% by weight and most preferably 0.05 to 0.2% by weight, based in each case on the polymer particles.

In a preferred embodiment of the present invention, cations, preferably polyvalent cations, are applied to the particle surface in addition to the surface postcrosslinkers before, during or after the surface postcrosslinking.

The cations or polyvalent cations usable in the process according to the invention are, for example, ammonium, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate, citrate, lactate, lactamide, glycinate, glycolate, 3-hydroxypropionate, methanesulfonate, methanesulfonamide, and also counterions described in patent application WO 2012/045705 A1, and mixtures thereof.

Aluminum sulfate, aluminum lactate and zirconium acetate are preferred. Apart from metal salts, it is also possible to use polyamines as polyvalent cations.

In a further embodiment, it is possible to generate organic salts from the cations and the counterions by separate addition in the various process steps, such as before, during or after the surface postcrosslinking. The addition can be effected in any sequence. Particularly preferred are cations are ammonium, and also the cations of aluminum and of zirconium. Useful organic counterions preferably include carboxylates, such as acetate, lactate, glycolate, citrate, in the form of the free acid and of the salts, and carboxamides, such as lactamide, glycinate.

The amount of polyvalent cation used is, for example, 0.001 to 1.5% by weight, preferably 0.005 to 1% by weight and more preferably 0.02 to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati;

USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water, propylene glycol/water and ethylene carbonate/water, where the mixing ratio in terms of mass is preferably from 20:80 to 40:60.

The surfactants used here are preferably the inventive surfactants and surfactant mixtures.

The thermal drying is preferably carried out in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The drying can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred drying temperatures are in the range of 100 to 250° C., preferably 120 to 220° C., more preferably 130 to 210° C. and most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, surfactants, such as Span® 20, and the inventive surfactants and surfactant mixtures.

The process according to the invention enables the production of water-absorbing polymer particles with a very low content of residual monomers.

The present invention further provides the water-absorbing polymer particles obtainable by the process according to the invention.

The water-absorbing polymer particles obtainable by the process according to the invention have a centrifuge retention capacity (CRC) of typically at least 15 g/g, preferably at least 20 g/g, more preferably at least 25 g/g, especially preferably at least 30 g/g and most preferably at least 35 g/g. The centrifuge retention capacity (CRC) of the water-absorbing polymer particles is typically less than 100 g/g.

The water-absorbing polymer particles obtainable by the process according to the invention have a residual monomer content of typically less than 0.5% by weight, preferably less than 0.3% by weight, more preferably less than 0.2% by weight and most preferably of less than 0.15% by weight.

The water-absorbing polymer particles obtainable by the process according to the invention have a moisture content of preferably at least 5% by weight, more preferably of at least 10% by weight and most preferably of at least 14% by weight.

The mean diameter of the water-absorbing polymer particles obtainable by the process according to the invention is preferably at least 200 μm, more preferably from 250 to 600 μm and very particularly from 300 to 500 μm, the particle diameter being determinable by light scattering and signifying the volume-average mean diameter. 90% of the polymer particles have a diameter of preferably 100 to 800 μm, more preferably of 150 to 700 μm, most preferably of 200 to 600 μm.

The present invention further provides hygiene articles comprising inventive water-absorbing polymer particles. The production of the hygiene articles is described in the monograph "Modern Superabsorbent Polymer Technology", F. L. Buchholz and A. T. Graham, Wiley-VCH, 1998, pages 252 to 258.

The hygiene articles typically comprise a water-impervious backside, a water-pervious topside and an intermediate absorbent core composed of the inventive water-absorbing polymer particles and fibers, preferably cellulose. The proportion of the inventive water-absorbing polymer particles in the absorbent core is preferably 20 to 100% by weight and more preferably 50 to 100% by weight.

The water-absorbing polymer particles are tested by means of the test methods described below.

Methods:

The measurements should, unless stated otherwise, be conducted at an ambient temperature of 23±2° C. and a relative air humidity of 50±10%. The water-absorbing polymers are mixed thoroughly before the measurement.

Residual Monomers

The residual monomer content of the water-absorbing polymer particles is determined by EDANA recommended test method WSP No. 210.2-05 "Residual Monomers".

Moisture Content

The moisture content of the water-absorbing polymer particles is determined by EDANA recommended test method No. WSP 230.2-05 "Mass Loss Upon Heating".

Centrifuge Retention Capacity

The centrifuge retention capacity (CRC) is determined by EDANA recommended test method No. WSP 241.2-05 "Fluid Retention Capacity in Saline, After Centrifugation".

Absorption Under a Pressure of 21.0 g/cm$^2$

The absorption under a pressure of 21.0 g/cm$^2$ (AUL0.3psi) of the water-absorbing polymer particles is determined by EDANA recommended test method No. WSP 242.2-05 "Absorption Under Pressure, Gravimetric Determination".

Absorption Under a Pressure of 0.0 g/cm²

The absorption under a pressure of 0.0 g/cm² (AUL0.0psi) is determined analogously to EDANA recommended test method No. WSP 242.2-05 "Absorption Under Pressure, Gravimetric Determination", except that a pressure of 0.0 g/cm² (AUL0.0psi) is established rather than a pressure of 21.0 g/cm² (AUL0.3psi).

Absorption Under a Pressure of 49.2 g/cm²

The absorption under a pressure of 49.2 g/cm² (AUL0.7psi) is determined analogously to EDANA recommended test method No. WSP 242.2-05 "Absorption Under Pressure, Gravimetric Determination", except that a pressure of 49.2 g/cm² (AUL0.7psi) is established rather than a pressure of 21.0 g/cm² (AUL0.3psi).

Bulk Density

The bulk density is determined by EDANA recommended test method No. WSP 260.2-05 "Density, Gravimetric Determination".

Extractables

The content of extractables of the water-absorbing polymer particles is determined analogously to EDANA recommended test method No. WSP 270.2-05 "Extractable". The extraction time is 16 hours.

Free Swell Rate

To determine the free swell rate (FSR), 1.00 g (=W1) of the water-absorbing polymer particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=W2). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/gs]=W2/(W1 \times t)$$

If the moisture content of the water-absorbing polymer particles, however, is more than 3% by weight, the weight W1 should be corrected to take account of this moisture content.

CIE Color Number (L, a, b)

The color analysis is carried out according to the CIELAB method (Hunterlab, volume 8, 1996, book 7, pages 1 to 4) with a "LabScan XE S/N LX17309" colorimeter (Hunter-Lab, Reston, US).

This method describes the colors via the coordinates L, a and b of a three-dimensional system. L indicates the brightness, where L=0 means black and L=100 white. The values of a and b indicate the positions of the color on the red/green and yellow/blue color axes respectively, where +a represents red, −a represents green, +b represents yellow and −b represents blue. The HC60 is calculated by the formula HC60=L−3b.

The color measurement corresponds to the three-area method according to DIN 5033-6.

The EDANA test methods are obtainable, for example, from EDANA, Avenue Eugène Plasky 157, B-1030 Brussels, Belgium.

EXAMPLES

Production of the Base Polymer

Example 1

Figure 1:
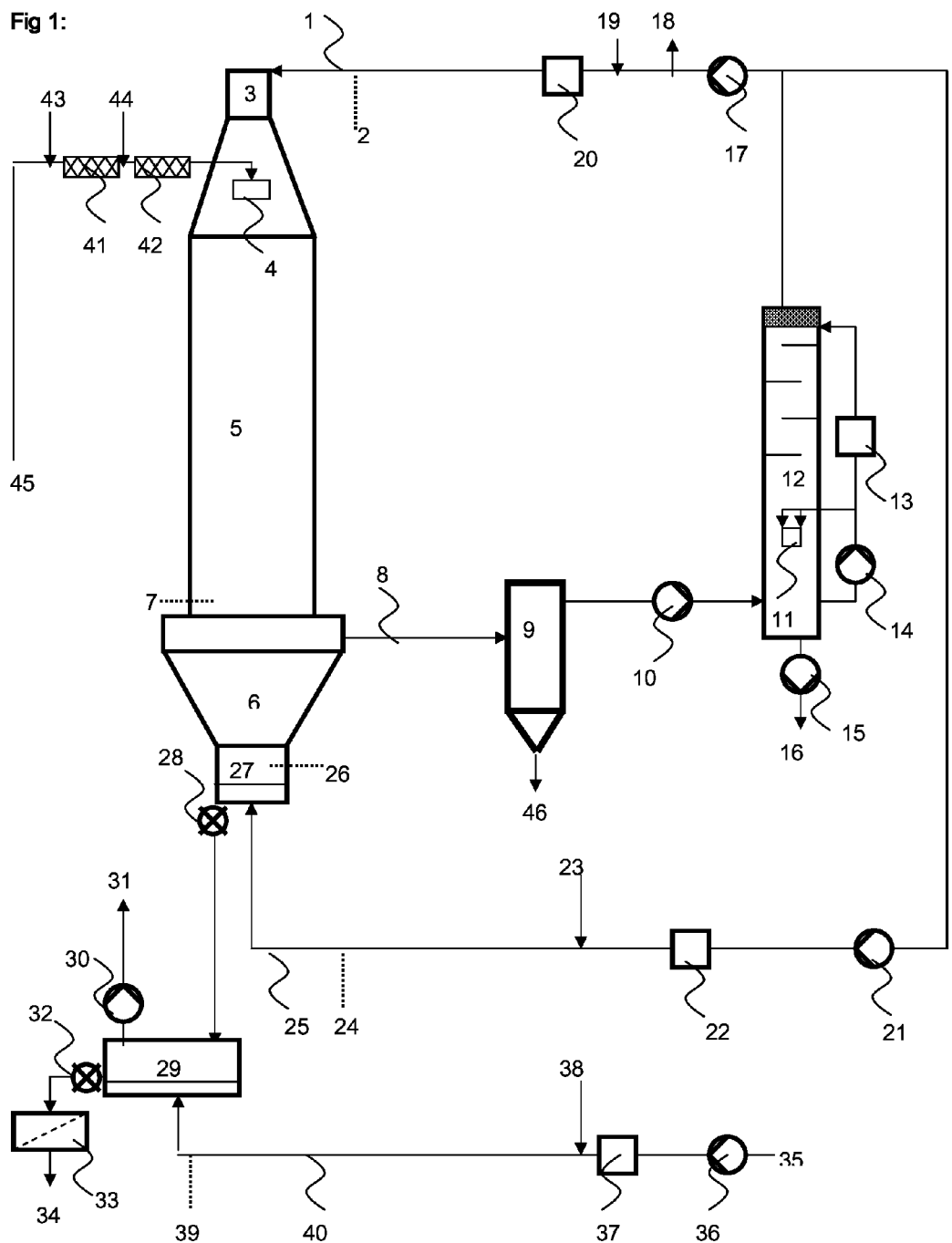
FIGS. 1-5 show the schematics of the apparatus for the process of removing residual monomers from the water-absorbing polymer particles.
Figure 2:
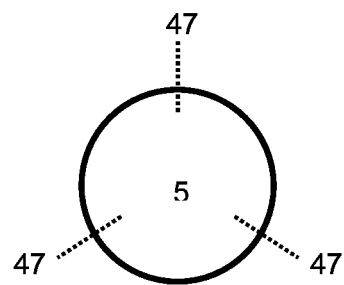

The process was performed in a spray drying system with integrated fluidized bed (27) and an external fluidized bed (29), as shown in FIG. 1 of WO 2011/026876 A1. The cylindrical portion of the spray drier (5) had a height of 22 m and a diameter of 3.4 m. The internal fluidized bed (IFB) had a diameter of 3 m and a weir height of 0.25 m. The external fluidized bed (EFB) had a length of 3.0 m, a width of 0.65 m and a weir height of 0.5 m.

The drying gas was supplied at the upper end of the spray drier via a gas distributor (3). The drying gas was partly recycled through a fabric filter (9) and a scrubbing column (12) (cycle gas). The drying gas used was nitrogen with an oxygen content of 1 to 4% by volume. Prior to commencement of the polymerization, the plant was purged with nitrogen down to an oxygen content of below 4% by volume. The gas velocity of the drying gas in the cylindrical portion of the spray drier (5) was 0.8 m/s. The pressure within the spray drier was 4 mbar below ambient pressure.

Figure 3:
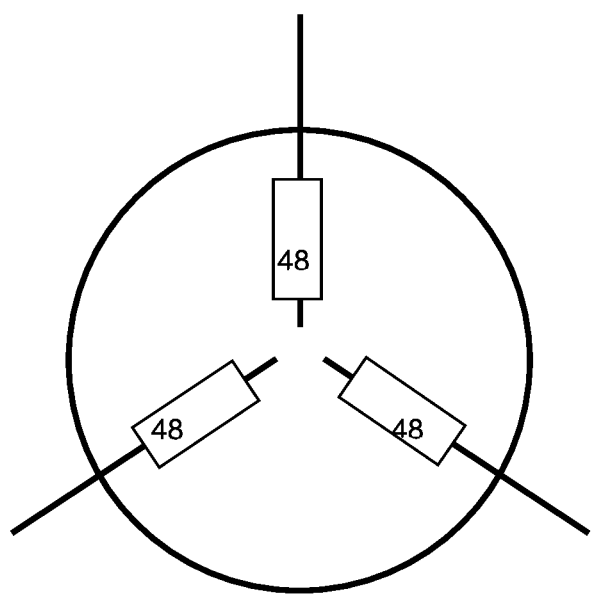

The starting temperature of the spray drier was measured at three points at the lower end of the cylindrical portion, as shown in FIG. 3 of WO 2011/026876 A1. The three individual measurements (47) were used to calculate the mean outlet temperature. The cycle gas was heated and the metered addition of monomer solution was commenced. From this time onward, the mean outlet temperature was regulated at 117° C. by adjustment of the gas inlet temperature by means of the heat exchanger (20).

The product was collected in the internal fluidized bed (27) up to the height of the weir. Via line (25), drying gas was supplied to the internal fluidized bed (25) with a temperature of 122° C. and a relative moisture content of 4%. The gas velocity in the internal fluidized bed (27) was 0.65 m/s. The residence time of the product in the internal fluidized bed (27) was 120 minutes.

The offgas of the spray drier was supplied to the scrubbing column (12) via the fabric filter (9). The liquid level within the scrubbing column (12) was kept constant by pumping out excess liquid. The liquid within the scrubbing column (12) was cooled by means of the heat exchanger (13) and conveyed in countercurrent through the nozzles (11), such that the temperature within the scrubbing column (12) was regulated to 45° C. In order to scrub acrylic acid out of the offgas, the liquid in the scrubbing column (12) was alkalized by addition of sodium hydroxide solution.

The offgas from the scrubbing column was divided between lines (1) and (25). The temperatures were regulated by means of the heat exchangers (20) and (22). The heated drying gas was supplied to the spray drier via the gas distributor (3). The gas distributor consisted of a row of plates and had a pressure drop of 2 to 4 mbar according to the gas rate.

The product was transferred from the internal fluidized bed (27) by means of the rotary feeder (28) into the external fluidized bed (29). Via line (40), drying gas was supplied to the external fluidized bed (29) with a temperature of 60° C. The drying gas was air. The gas velocity in the external fluidized bed (29) was 0.8 m/s. The residence time of the product in the external fluidized bed (29) was 1 minute.

The product was transferred from the external fluidized bed (29) by means of the rotary feeder (32) onto the sieve (33). By means of the sieve (33), particles with a particle size of greater than 800 μm (agglomerates) were removed.

Figure 4:
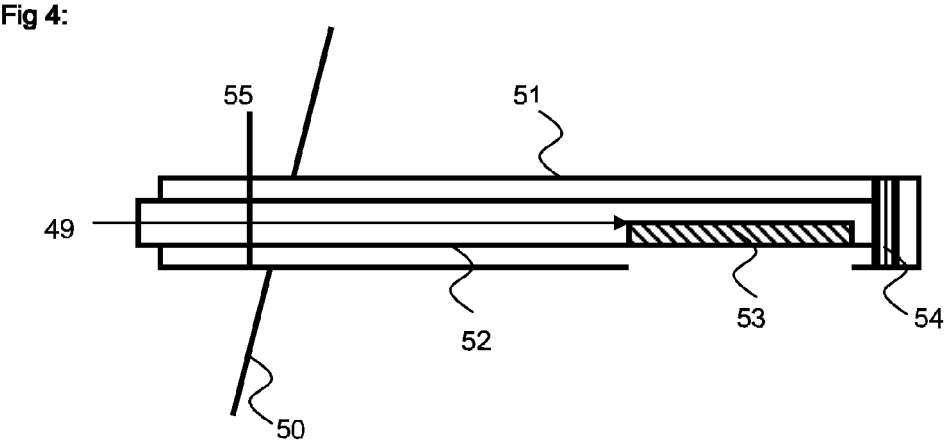

To prepare the monomer solution, freshly distilled acrylic acid was admixed first with triethoxylated glyceryl triacrylate (crosslinker) and then with 37.3% by weight aqueous sodium acrylate. By pumped circulation through a heat exchanger, the temperature of the monomer solution was kept at 10° C. In the pumped circulation system, a filter with a mesh size of 250 μm was disposed beyond the pump. The initiators were added to the monomer solution via lines (43) and (44) upstream of the static mixers (41) and (42). Sodium peroxodisulfate was supplied with a temperature of 20° C. via line (43), and a mixture of [2,2'-azobis[2-(2-imidazolin-2-yl)propane]dihydrochloride and Brüggolit® FF7 (Brüggemann Chemicals; Heilbronn; Germany) was supplied with a temperature of 5° C. via line (44). Each initiator was pumped in circulation and metered via regulating valves in each dropletizer unit. Beyond the static mixer (42) was disposed a filter with a mesh size of 140 μm. For metered addition of the monomer solution at the tip of the spray drier, three dropletizer units were used, as shown in FIG. 4 of WO 2011/026876 A1.

Figure 5:
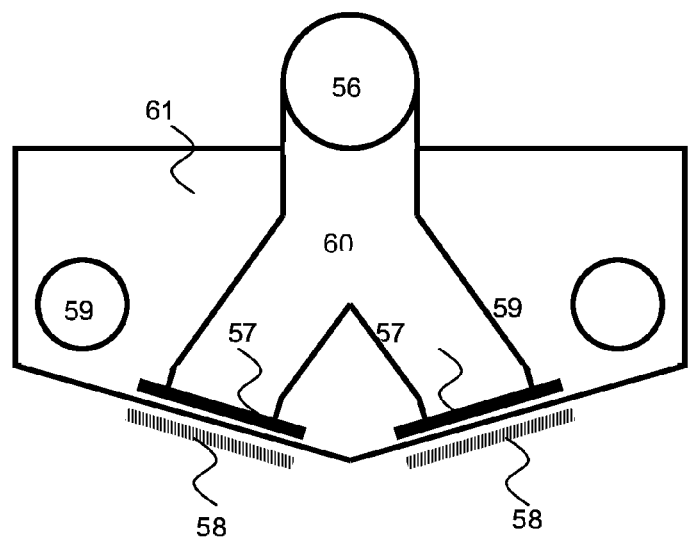

One dropletizer unit consisted of an outer tube (51) and a dropletizer cartridge (53), as shown in FIG. 5 of WO 2011/026876 A1. The dropletizer cartridge (53) was connected by an inner tube (52). The inner tube (52) had a PTFE seal (54) at the end and could be pulled out for maintenance purposes during operation.

The temperature of the dropletizer cartridge (61) was regulated to 8° C. by means of cooling water in the channels (59), as shown in FIG. 6 of WO 2011/026876 A1. The dropletizer cartridge (61) had 256 holes with a diameter of 170 μm and a distance between the holes of 15 mm. The dropletizer cartridge (61) had a flow channel (60) free of dead spaces for homogeneous distribution of the premixed monomer solution and of the initiator solutions between the two dropletizer plates (57). The two dropletizer plates (57) had an angled arrangement with an angle of 3°. Each dropletizer plate (57) was made of stainless steel (materials No. 1.4571) and had a length of 500 mm, a width of 25 mm and a thickness of 1 mm.

The feed to the spray drier comprised 10.45% by weight of acrylic acid, 33.40% by weight of sodium acrylate, 0.018% by weight of triethoxylated glyceryl triacrylate (purity approx. 85% by weight), 0.036% by weight of [2,2'-azobis[2-(2-imidazolin-2-yl)propane]dihydrochloride, 0.0029% by weight of Brüggolit® FF7 (Brüggemann Chemicals; Heilbronn; Germany), 0.054% by weight of sodium peroxodisulfate and water. Brüggolit® FF7 was used in the form of a 5% by weight aqueous solution and sodium peroxodisulfate was used in the form of a 15% by weight aqueous solution. The degree of neutralization was 71%. The feed per hole was 1.6 kg/h.

The resulting polymer particles had the following properties:
CRC of 32.6 g/g
AUL0.0psi of 37.5 g/g
AUL0.3psi of 24.2 g/g
AUL0.7psi of 12.0 g/g
extractables of 4.0% by weight
residual monomers 15 100 ppm
moisture content of 6.1% by weight
FSR of 0.28 g/gs
HC60 of 91.1
Color values: L=95.0/a=2.2/b=1.3

The resulting polymer particles had a bulk density of 0.74 g/ml and an average particle diameter of 381 μm.

Example 2

The preparation was effected analogously to example 1. The feed to the spray drier comprised 10.45% by weight of acrylic acid, 33.40% by weight of sodium acrylate, 0.018% by weight of triethoxylated glyceryl triacrylate (purity approx. 85% by weight), 0.072% by weight of [2,2'-azobis[2-(2-imidazolin-2-yl)propane]dihydrochloride, 0.0029% by weight of Brüggolit® FF7 (Brüggemann Chemicals; Heilbronn; Germany), 0.054% by weight of sodium peroxodisulfate and water. Brüggolit® FF7 was used in the form of a 5% by weight aqueous solution and sodium peroxodisulfate was used in the form of a 15% by weight aqueous solution. The degree of neutralization was 71%. The feed per hole was 1.6 kg/h.

The resulting polymer particles had the following properties:
CRC of 47.0 g/g
AUL0.0psi of 55.1 g/g
AUL0.3psi of 25.1 g/g
AUL0.7psi of 7.6 g/g
extractables of 3.8% by weight
residual monomers 11 700 ppm
moisture content of 6.1% by weight
FSR of 0.14 g/gs
HC60 of 92.5
Color values: L=96.1/a=1.7/b=1.2

The resulting polymer particles had a bulk density of 0.75 g/ml and an average particle diameter of 385 μm.

Thermal Aftertreatment

Comparative Examples CE1 and 2 and Examples 3 to 12

1.5 kg of water-absorbing polymer particles from example 1 were thermally aftertreated in an M5R plowshare mixer (Gebr. Lödige Maschinenbau GmbH; Paderborn; Germany).

For this purpose, the plowshare mixer was preheated to a wall temperature of 100° C. for one hour. After heating, the water-absorbing polymer particles from example 1 were introduced into the plowshare mixer. Subsequently, the motor was started and the speed was set to 60 rpm. After a heating time of 20 minutes, the first half of the spray substance according to table 1, which had been heated to about 80° C., was sprayed by means of a Büchi two-phase nozzle onto the product from above with 1 bar nitrogen within 6.5 minutes. Subsequently, stirring was continued for 5 minutes and then the second half of the spray substance was sprayed on under analogous conditions. The product was stirred at a temperature of 80° C. for a further 30 minutes. In the course of this, a nitrogen stream of 60 l/h was passed through the plowshare mixer. The cooled product was sieved to <850 μm on an AS400 sieve shaker (Retsch GmbH; Haan; Germany).

Comparative Example CE3 and Examples 13 to 15

45 kg of water-absorbing polymer particles from example 2 were thermally aftertreated in an FM130 plowshare mixer (Gebr. Lödige Maschinenbau GmbH; Paderborn; Germany). Over the entire experiment, the speed of the plowshare mixer was 60 rpm and the power consumption 6.4 to 6.5 W. About 10 m$^3$ (STP)/h of nitrogen flowed through the mixing space at absolute supply pressure about 3 bar and a gas temperature of 180° C. The Froude number was 0.93.

Before filling the mixing space, the plowshare mixer was preheated to a jacket temperature of 150° C. Subsequently, the water-absorbing polymer particles from example 2 were introduced into the plowshare mixer and heated while stirring for 20 minutes. The product temperature rose to 70° C.

In the next step, the nitrogen was combined with an amount of steam of about 6.5 kg/h. The amount of steam was regulated so as to establish a relative gas moisture content of 30%. The gas moisture content was determined by means of a HydroFlex moisture meter (Rotronic Messgeräte GmbH; Nuremberg; Germany). The gas temperature was 180° C. During this time, according to table 2, water was sprayed on in 4 equal portions at a temperature of 25° C. by means of a 970S4 1.2 mm two-phase nozzle (Düsen-Schlick GmbH; Untersiemau; Germany), each within 8 minutes. The two-phase nozzle was operated with nitrogen (3 bar).

At the end of the spraying operation, the product had a temperature of about 85° C. The steam loading and the nitrogen heating were switched off. The product was then further dried while stirring for a total of 15 minutes. Shortly before emptying, the product had a temperature of about 76° C.

After the experiment had ended, the cooled product was divided and sieved to <850 μm on an AS400 sieve shaker (Retsch GmbH; Haan; Germany).

TABLE 1

| Ex. | Spray substance | Particles >850 μm [% by wt.] | Agglomerates [% by wt.] | Moisture content [% by wt.] | Residual monomers [ppm] |
|---|---|---|---|---|---|
| 1 | — | 3.1 | 0 | 6.1 | 16000 |
| CE1 | 225 g water | 30.4 | 27.3 | 10.7 | 2400 |
| CE2 | 225 g water + 0.15 g Span20 | 22.4 | 19.3 | 11.9 | 1700 |
| 3 | 225 g water + 0.15 g Plantacare 818UP | 5.2 | 2.1 | 12.3 | 1100 |
| 4 | 225 g water + 0.15 g Plantacare 1200UP | 8.9 | 5.8 | 12.3 | 1100 |
| 5 | 225 g water + 0.15 g Plantacare K55 | 12.9 | 9.8 | 14.3 | 1800 |
| 6 | 225 g water + 0.15 g Euperlan PCO | 10.8 | 7.7 | 11.5 | 1100 |
| 7 | 225 g water + 0.15 g Lutensol AO7 | 13.8 | 10.7 | 9.3 | 2800 |
| 8 | 225 g water + 0.15 g Lutensol XL70 | 13.9 | 10.8 | 9.3 | 3400 |
| 9 | 225 g water + 0.15 g Lutensol FA12K | 14.7 | 11.6 | 10.1 | 2200 |
| 10 | 225 g water + 0.15 g Arquad 2HT-75 | 5.7 | 2.6 | 9.8 | 2600 |
| 11 | 225 g water + 0.15 g Emulan EL40 | 12.8 | 9.7 | 9.8 | 2500 |
| 12 | 225 g water + 0.15 g Luviquat Mono CP | 2.6 | 0.0 | 12.5 | 2000 |

TABLE 2

| Ex. | Spray substance | Particles >850 μm [% by wt.] | Agglomerates [% by wt.] | Moisture content [% by wt.] | Residual monomers [ppm] | Surface tension [mN/m] |
|---|---|---|---|---|---|---|
| 2 | | 3.3 | | 6.3 | 11680 | 72.0 |
| CE3 | 4 × (843 g water) | 31.3 | 28.8 | 9.7 | 2100 | 71.8 |
| 13 | 4 × (843 g water + 1.125 g Plantacare 818UP) | 4.2 | 0.6 | 8.9 | 1200 | 72.1 |
| 14 | 4 × (843 g water + 2.25 g Plantacare 818UP) | 2.1 | 0.0 | 9.3 | 900 | 70.9 |
| 15 | 4 × (843 g water + 3.375 g Luviquat Mono CP) | 3.5 | 0.2 | 8.8 | 1000 | 64.7 |

The surfactants used have been the following compounds:

Span®20 (sorbitan monooctoate, Croda International Plc, CAS No. CAS 1338-39-2)

Plantacare®818UP (approx. 52% by weight aqueous solution of cocoglycoside, BASF SE, CAS No. 110615-47-9/68515-73-1)

Plantacare®1200UP (approx. 50% by weight aqueous solution of lauryl glycoside, BASF SE, CAS No. CAS No. 110615-47-9)

Plantacare®K55 (approx. 47% by weight aqueous solution of a mixture of lauryl glycoside and cocoamidopropyl betaine, BASF SE, CAS No. CAS No. 110615-47-9/61789-40-0)

Plantacare®PS10 (approx. 60% by weight aqueous solution of a mixture of sodium laurether sulfate and lauryl glycoside, BASF SE, CAS No. 110615-47-9/68891-38-3)

Euperlan®PCO (approx. 43% by weight dispersion of a mixture of styrene/acrylate copolymer with cocoglycoside, BASF SE)

Lutensol®AO7 (ethoxylated oxo alcohol, BASF SE): Lutensol®AO7 is a nonionic liquid surfactant based on a saturated $C_{13}/C_{15}$ oxo alcohol which consists of about 67% $C_{13}$ oxo alcohol and about 33% $C_{15}$ oxo alcohol and is predominantly unbranched. The composition of Lutensol®AO7 is described by the following general structural formula: $RO(CH_2CH_2O)_7H$ where $R=C_{13}/C_{15}$ oxo alcohol. Lutensol®AO7 has a viscosity of about 100 mPas, an HLB value of about 12 and an active content of 100%.

Lutensol®XL70 (ethoxylated Guerbet alcohol, BASF SE): Lutensol®XL70 is a nonionic liquid surfactant based on a $C_{10}$ Guerbet alcohol. The composition of Lutensol®XL70 is described by the following general structural formula: $RO(CH_2CH_2O)_7H$ where $R=C_{10}$ Guerbet alcohol. Lutensol®XL70 has a viscosity of about 70 mPas, an HLB value of about 13 and an active content of 100%.

Lutensol®FA12K (ethoxylated cocoalkylamine, BASF SE): Lutensol®FA12K is a nonionic liquid surfactant based on cocoamine. The composition of Lutensol®FA12K is described by the following general structural formula: $R—N[(CH_2CH_2O)_6H]_2$ where $R—NH_2$=cocoamine. Lutensol®FA12K has a viscosity of about 190 mPas and an active content of 100%.

Arquad®2HT-75 (ditallowdimethylammonium chloride, AkzoNobel GmbH, CAS No. 61789-80-8)

Emulan®EL40 (ethoxylated castor oil, BASF SE): Emulan®EL40 is a nonionic liquid surfactant based on castor oil. The composition of Emulan®EL40 is described by the following general structural formula: $ROCH_2CH(OR)CH_2OR$ where $R=H_3C(CH_2)_5CH[O(CH_2CH_2O)_{40/3}H]CH_2CH=CH(CH_2)_7COO—$. Emulan®EL40 has a viscosity of about 3000 mPas, an HLB value of about 12 and an active content of 100%.

Luviquat®Mono CP (approx. 30% by weight aqueous solution of hexadecyl(2-hydroxyethyl)dimethylammonium dihydrogenphosphate, BASF SE, CAS No. 85563-48-0)

The invention claimed is:

1. A process for removing residual monomers from water-absorbing polymer particles by thermally aftertreating the water-absorbing polymer particles in a mixer having rotating mixing tools, the water-absorbing polymer particles during the thermal aftertreatment having a temperature of at least 60° C. and a water content of at least 8% by weight, with addition of water or an aqueous solution before or during the thermal aftertreatment and/or of a steam-comprising gas stream during the thermal aftertreatment, wherein process comprises performing the thermal aftertreatment in the presence of at least one surfactant, the at least one surfactant having a polar group and a nonpolar group, the polar group and the nonpolar group of the surfactant not being joined via a carboxylic ester group, and the polar group having at least one hydroxyl group, a cationic group, or an anionic group and the nonpolar group having a $C_4$- to $C_{20}$-alkyl chain.

2. The process according to claim 1, wherein the polar group is a cationic group.

3. The process according to claim 1, wherein the surfactant is a surfactant mixture.

4. The process according to claim 3, wherein surfactants in the surfactant mixture comprise different linear and/or branched alkyl chains as nonpolar groups.

5. The process according to claim 1, wherein from 0.0005 to 0.01% by weight of the at least one surfactant, based on the water-absorbing polymer particles, is used.

6. The process according to claim 1, wherein the water-absorbing polymer particles have a temperature of 80 to 110° C. during the thermal aftertreatment.

7. The process according to claim 1, wherein from 0.05 to 20% by weight of water or an aqueous solution is added before or during the thermal aftertreatment, based on the water-absorbing polymer particles.

8. The process according to claim 1, wherein the gas stream added during the thermal aftertreatment comprises from 0.05 to 1.0 kg of steam per kg of dry gas.

9. The process according to claim 1, wherein a mean residence time in the mixer is from 10 to 120 minutes.

10. The process according to claim 1, wherein a gas volume used for thermal aftertreatment in a batchwise mixer is from 0.01 to 5 m$^3$ (STP)/h per kg of water-absorbing polymer particles, or, in a continuous mixer, from 0.01 to 5 m$^3$ (STP)/h per kg/h of water-absorbing polymer particle throughput.

11. The process according to claim 1, wherein the thermal aftertreatment is performed in a horizontal mixer.

12. The process according to claim 1, wherein the water-absorbing polymer particles are prepared by polymerizing a monomer solution comprising
a) at least one ethylenically unsaturated monomer which bears an acid group and optionally is at least partly neutralized,
b) at least one crosslinker,
c) at least one initiator,
d) optionally one or more ethylenically unsaturated monomer copolymerizable with the monomer mentioned under a),
e) optionally one or more water-soluble polymer or copolymer and
f) water.

13. The process according to claim 12, wherein the monomer a) has been neutralized to an extent of at least 25 mol %.

14. The process according to claim 12, wherein the monomer a) is acrylic acid to an extent of at least 50 mol %.

15. The process according to claim 12, wherein the monomer solution comprises at least 0.1% by weight of crosslinker b), based on unneutralized monomer a).

* * * * *